United States Patent [19]

Bulley et al.

[11] Patent Number: 5,499,966
[45] Date of Patent: Mar. 19, 1996

[54] TUBULAR BANDAGES

[75] Inventors: John L. Bulley, Padstow; Stephen I. Gradwell, St. Columb Major, both of England

[73] Assignee: JLB Textiles Limited, Cornwall, England

[21] Appl. No.: 196,157

[22] PCT Filed: Aug. 18, 1992

[86] PCT No.: PCT/GB92/01521

§ 371 Date: Apr. 20, 1994

§ 102(e) Date: Apr. 20, 1994

[87] PCT Pub. No.: WO93/03691

PCT Pub. Date: Mar. 4, 1993

[30] Foreign Application Priority Data

Aug. 21, 1991 [GB] United Kingdom .................. 9118062

[51] Int. Cl.$^6$ ............................ A61F 13/00; A61F 15/00
[52] U.S. Cl. ................................. 602/42; 602/41
[58] Field of Search .................. 602/1, 7, 8, 22, 602/30, 42–45, 51, 53–55, 48, 60–63; 128/856

[56] References Cited

U.S. PATENT DOCUMENTS

| | | | |
|---|---|---|---|
| 2,571,946 | 10/1951 | Rosenfield | 602/63 X |
| 4,202,331 | 5/1980 | Yale . | |
| 4,630,603 | 12/1986 | Greenway | 602/45 |
| 4,664,662 | 5/1987 | Webster | 602/47 |
| 4,671,266 | 6/1987 | Lengyel et al. | 602/45 |
| 4,838,253 | 6/1989 | Brassington et al. | 602/47 X |
| 4,926,851 | 5/1990 | Bulley | 128/856 X |
| 5,010,883 | 4/1991 | Rawlings et al. | 602/52 |
| 5,052,380 | 10/1991 | Polta . | |
| 5,063,063 | 11/1991 | Miller | 602/43 X |

*Primary Examiner*—Linda C. M. Dvorak
*Attorney, Agent, or Firm*—Larson and Taylor

[57] ABSTRACT

A tubular bandage comprises a length of tubular-knitted fabric having one or more courses of substantially inelastic yarn interknitted with one or more courses of elastic yarn throughout said length, the bandage having a first end portion rolled inwardly from the free end and the other end portion rolled outwardly from the opposite free end to form two rolls, and there is incorporated in, associated with or otherwise applied to the tubular bandage, means which may serve to render the bandage impervious to fluids, may incorporate a microbial agent, may render the bandage supportive and/or may include a supporting structure such as a splint.

20 Claims, 5 Drawing Sheets

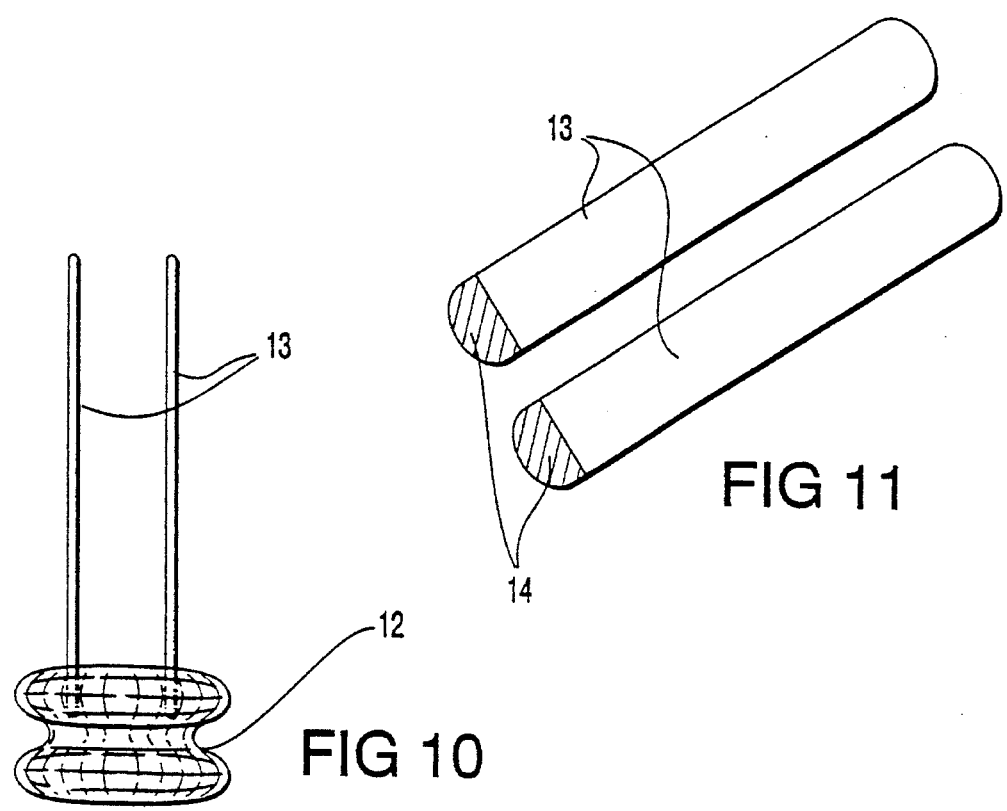
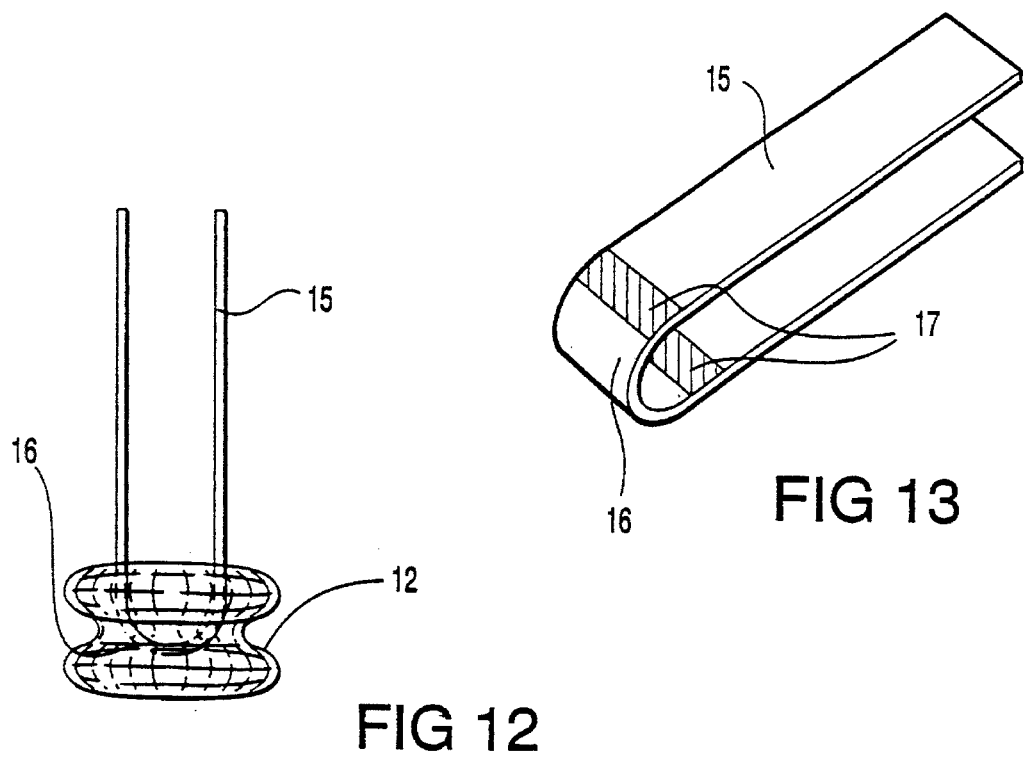

5,499,966

TUBULAR BANDAGES

FIELD OF THE INVENTION

The present invention relates to new tubular bandages, to a method of applying the bandages, to a method of manufacture of the bandages and to their use in both medical and veterinary fields.

BACKGROUND OF THE INVENTION

Tubular bandages are in common use and are available in a range of sizes suitable for use in bandaging anything from fingers to arms, legs and toes and even the head. The bandage material is normally supplied in a roll from which a suitable length is cut for use, this length being applied to the injured part to be bandaged with the aid of an applicator. Although the use of an applicator is not particularly difficult, it does need a certain amount of time and patience and also thought to replace the applicator with the unused roll of bandage so that it is available for subsequent use. A further problem with such bandages is that a "suitable" length must be cut from the roll for use: often substantially more than is actually needed for a particular job is cut off and considerable quantities of the roll are therefore wasted.

It is also known that an improved tubular bandage is available for use, this improved tubular bandage being manufactured in such a way that it is more easily applied to an injured part. The bandage referred to and available for use is a tubular bandage comprising a length of tubular-knitted fabric comprising courses of substantially inelastic yarn interknitted with courses of elastic yarn throughout said length, the bandage having a first end portion rolled outwardly from the free end and the other end portion rolled inwardly from the opposite free end to form two rolls.

This improved tubular bandage is applied to a body part by selecting a bandage as described above of a suitable size for the part, fitting the first end portion of the bandage around the body part, adjacent the section to be covered, unrolling the first end portion of the bandage so as to cover the body portion and subsequently unrolling the other end portion of the bandage over the first bandage portion so that the body part is in fact covered by two layers of the tubular bandage.

The provision of the improved bandages in pre-rolled form considerably facilitates their application to the injured part and avoids any need for an applicator. If the part to be bandaged comprises an extremity, such as a finger, once the first end of the bandage has been rolled into position, the centre of the bandage may be twisted, in known manner, before the other end of the bandage is rolled over the first portion so that the finger tip is fully covered. In the case of an intermediate part, such as the forearm, however, the bandage would not be twisted in this way. Although the improved tubular bandage referred to, consisting of a knitted fabric incorporating elastic and inelastic yarns, is suitable for many uses, it has now been found that the efficacy of the bandages when used for certain applications are improved if certain modifications are made as improvements, as defined in Claim 1 and the remainder of the claims appended to this specification.

SUMMARY OF THE INVENTION

For example, one such modification consists of the incorporation in or around the tubular bandage of a material which is suitable for direct application to that area of skin which has been damaged, destroyed or affected in such a way as to be unhealthy and which is suitable to promote cleansing, healing, growth of the skin or tissue where applied and/or to inhibit the growth and development of toxic materials, bacteria, fungi or other microbiological species.

This material may be chemical in nature, such as a cleansing agent, deodorising agent, antimicrobial agent, tissue-healing agent, growth promotion agent, agent to relieve pain, swelling or distortion of the tissue area, agent to promote skin blending during and/or after skin grafting, blood coagulating agent, anti-stick agent to prevent the tubular bandage adhering to the wound, for example silicones, and similar materials and flavouring agents.

Alternatively, or additionally, the material may be physical in nature, for example gauze, lint, tulle, fibre rovings, non-woven materials and fabrics all of which may optionally be impregnated with chemical and/or biological materials, including those mentioned above, for example silicones, sponge or foam strip (natural or synthetic), charcoal pad (as may be used for burns) which, when applied with or as part of the tubular bandage, forms a dressing for the wound or other non-normal skin or other tissue.

BRIEF DESCRIPTION OF THE DRAWINGS

Embodiments of the invention will now be described by way of example with reference to the accompanying drawings, of which

FIGS. 10 to 13 show ways in which a bandage may be attached to a supporting structure.

DESCRIPTION OF THE PREFERRED EMBODIMENTS

Figure 1:
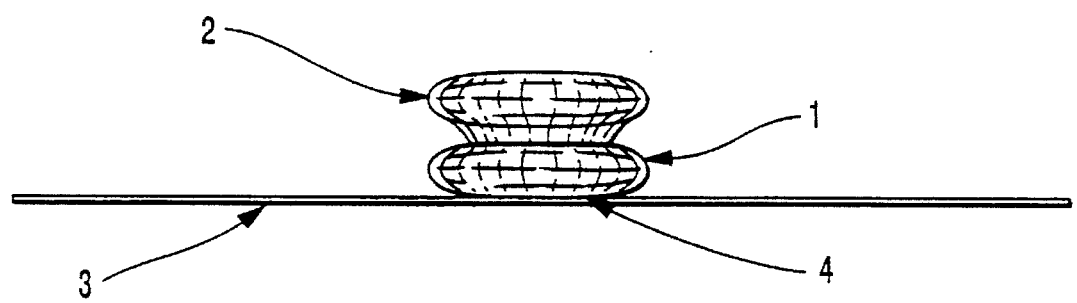
FIG. 1 is a side view of a tubular bandage in the rolled condition.
Figure 2:
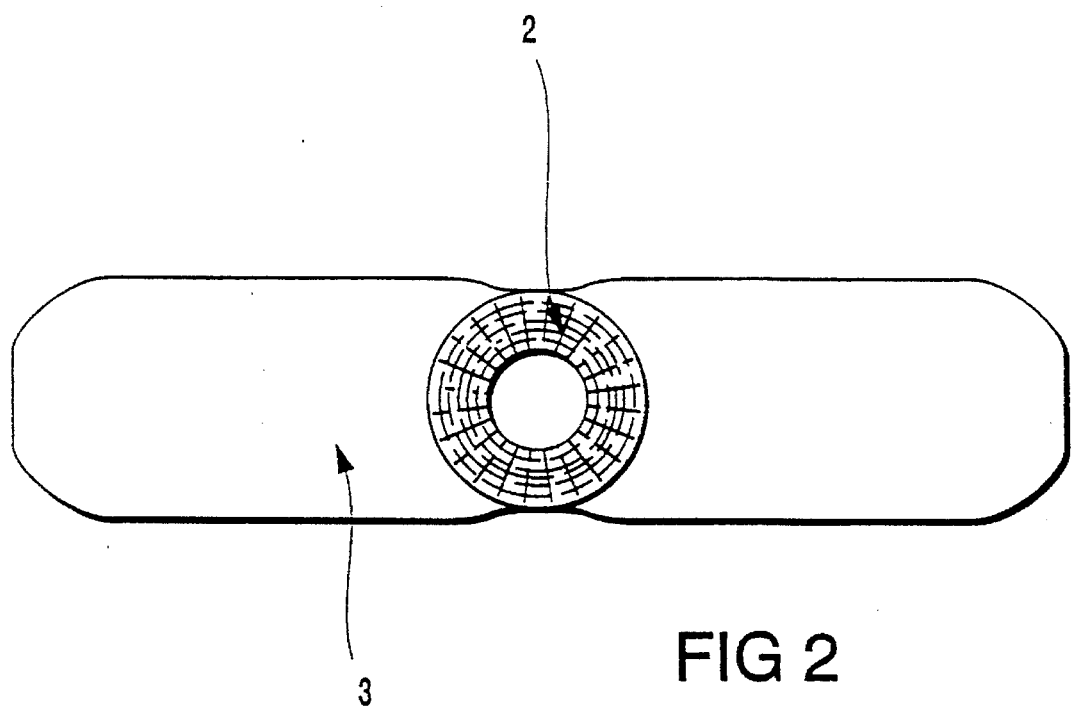
FIG. 2 is a plan view of the bandage of FIG. 1.

Referring to FIGS. 1 and 2, a tubular bandage is shown attached to a wound or tissue dressing, in which: 1 refers to the first roll of the tubular bandage, 2 refers to the second roll of the tubular bandage, 3 refers to the wound or tissue dressing, and 4 refers to a layer of non-toxic adhesive to attach the dressing to the tubular bandage.

The wound or tissue dressing, which may include gauze, may contain any of the chemical agents referred to above, or others, in amounts which are not detrimental to healing or growth promotion, for example those agents which are used in the treatment of infected wounds, those used for application to areas of burning or scalding or as other medical and surgical aids.

A further modification is the treatment of one or more surfaces of the material used to manufacture the tubular bandages so that the bandage when applied is resistant to the inward passage of water, oils, vapours or other fluids but optionally still allows passage outward of gases, for example air. In the practice of the invention, it is preferred to treat only one surface of the outer layer of bandage with the fluid-impervious composition and this may conveniently be carried out during the final stages of manufacture of the bandage, that is, during the rolling process. Also envisaged is a tubular bandage in which the first roll includes one or more of the chemical and/or biological agents mentioned above and the second roll is treated to be impervious to fluids and vapours. There are various methods of rendering the bandage fluid-proof but, by way of example, one is described herein, with particular reference to the finger bandage, and is illustrated in FIGS. 3, 4, 5 and 6.

Figure 4:
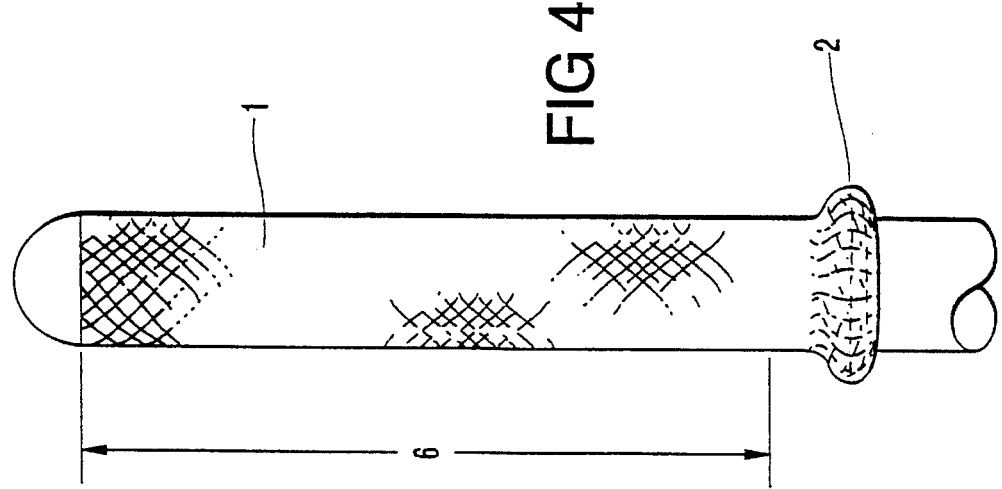
FIGS. 3 to 6 show a sequence of a method of rendering a finger bandage fluid-proof.
Figure 3:
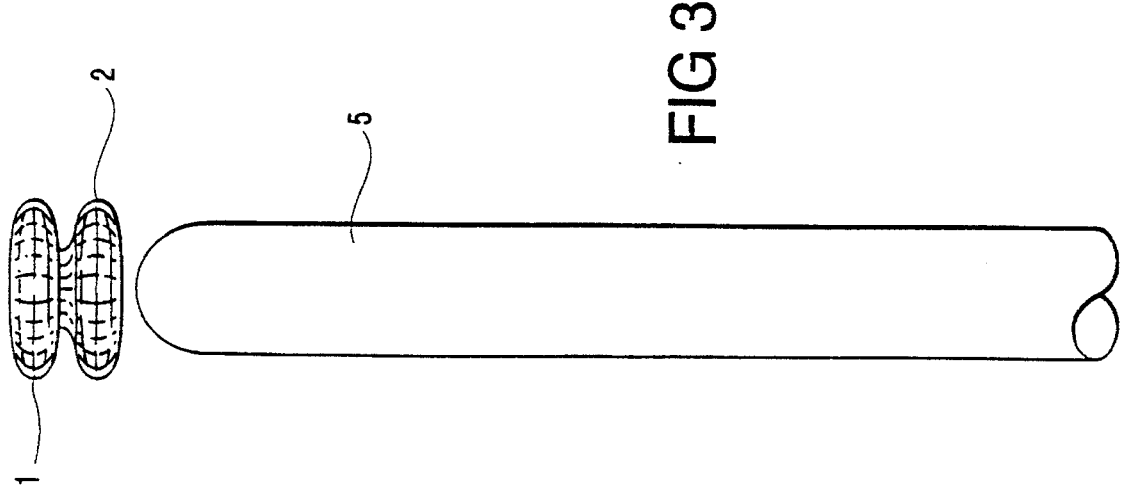
Figure 6:
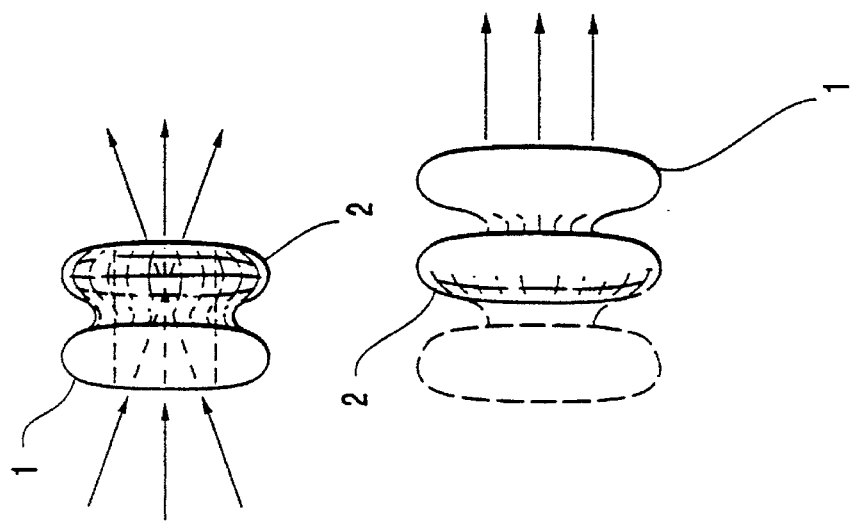
Figure 5:
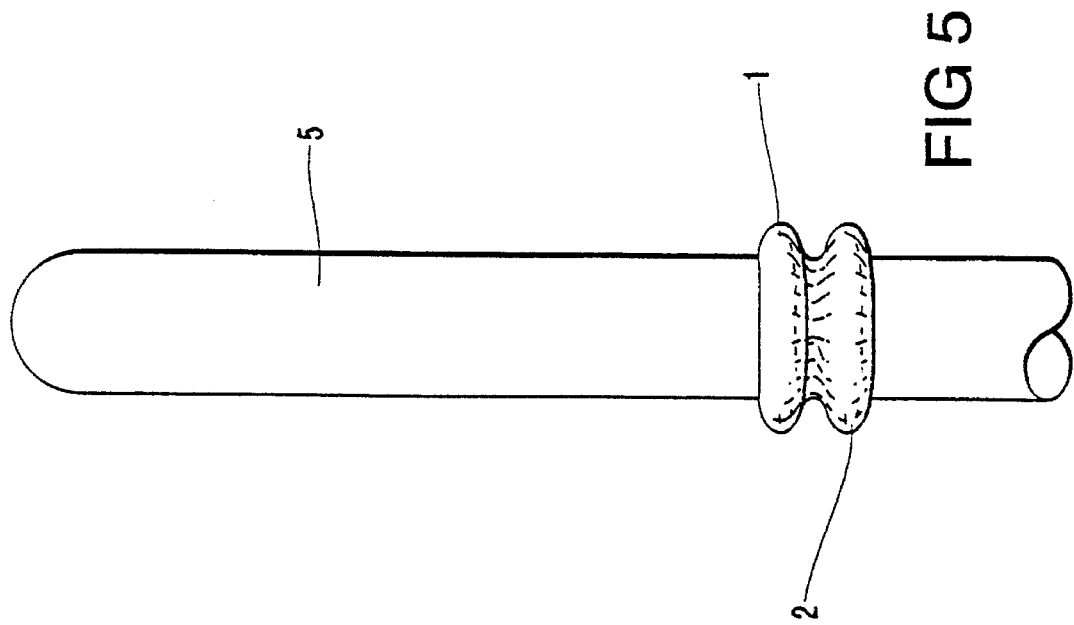

A completed tubular bandage, for example a finger bandage, the two rolls of which are indicated as 1 and 2, is applied over a former 5. The first roll 1 of the tubular bandage is then pulled up over the former, holding the second roll 2 at the lower end of the former, as shown in FIG. 4. The former over which the first roll of bandage has been unrolled is then dipped in a coating liquid, for example a liquid latex. The dip level is indicated at 6. After drying and curing as necessary, the coating is preferably treated with a material such as talc to prevent adhesion. The first roll is then rolled down again as in FIG. 5 and finally both first and second rolls simultaneously are removed from the former. The roll 1 which is coated with the fluid-impervious (barrier-type) material is then pushed through the other roll 2 in the direction of the arrows illustrated in FIG. 6.

Yet a further modification of the tubular bandage, especially when used for digits including toes, comprises the incorporation of means by which the unrolled bandage may be secured to the limb, such means including for example braid and/or thread attached to or incorporated during manufacture as part of the fabric of the bandage, or the association or attachment of some form of securing aid to the bandage, particularly to the larger bandages and to those used for veterinary purposes. This attachment agent may be applied in various forms; for example, it may be applied as a "pull-off" adhesive strip attached at a suitable part of the tubular bandage. Alternatively the securing aid may consist of a suitable non-irritant, non-toxic adhesive agent applied at the time of use of the bandage.

A further modification consists of the incorporation of different dyestuffs into certain of the fibres used to manufacture the tubular bandages, thereby producing coloured tubular bandages. These are particularly useful in certain industrial applications, for example, blue finger bandages for use on personnel working in the food industry. Various dyestuffs are suitable for use in this aspect of the invention provided they are non-toxic and non-carcinogenic. These dyestuffs carry various colours, but those have been found to be especially suitable are red, yellow, green, black, pink and blue, partly because of their colour-fastness and partly because of their "eye-appeal" especially to children. These coloured bandages are particularly suitable for use in childrens' hospitals. Alternatively, there may be printed onto the fabric of the tubular bandages, logos, words or other identifying or illustrative means, for example by jet printing; furthermore, reflective and/or reflective and/or fluorescent means for arms and legs may be incorporated.

Yet a further modification consists of a method of manufacture of sterilized tubular bandages and to methods of packaging such that the tubular bandages are maintained sterile. The tubular bandages may be available as individually wrapped/packed tubular bandages either singly or in the form of multi-strips or rolls suitable for hospitals, accident and emergency services, home health care, first aid and kits. These are shown diagrammatically in FIG. 7 and FIG. 8.

Figure 7A:
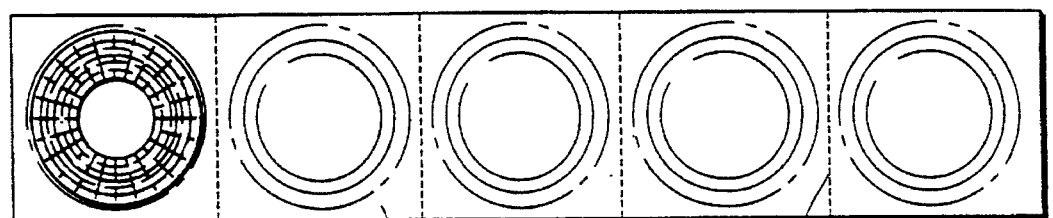
FIGS. 7A and 7B show respective plan and side views of one way of packaging individual bandages.
Figure 7B:

FIGS. 7A and 7B show individual tubular bandages packaged in a transparent polyester blister pack 7 in strips of five, the strip being suitably perforated at 8 for easy separation and individual pack opening. Preferably, the material of the blister pack is suitable for sterilization. The pack includes a heat-sealed backing strip 9.

Figure 8A:
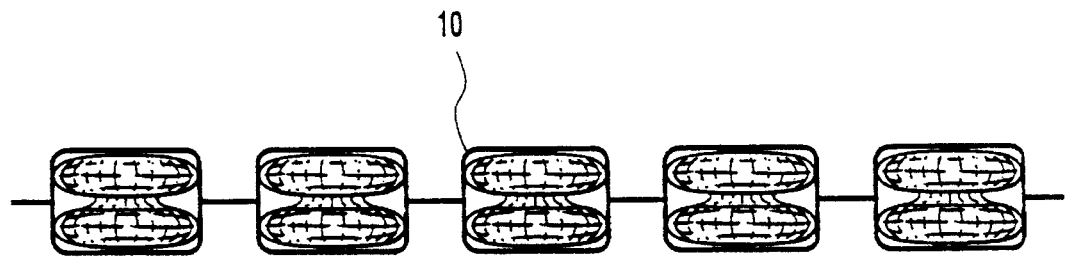
FIGS. 8A and 8B show respective side and plan views of another way of packaging individual bandages.
Figure 8B:
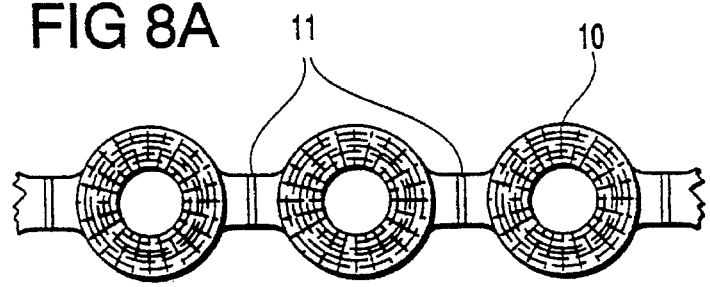
Figure 9:
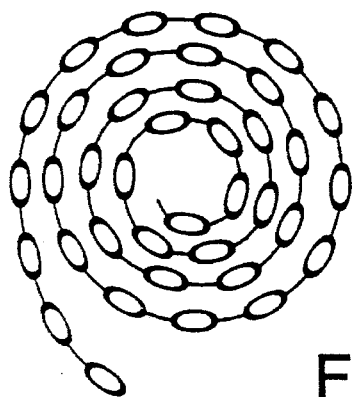
FIG. 9 shows packaged bandages formed in a roll.

FIGS. 8A and 8B show detachable individual tubular bandages packaged in a continuous strip 10, for example of polyethylene having heat-sealed separation zones 11 between individual bandages. The strip is suitable for wall-dispensing in rolls of varying lengths, for example for hospital use, as shown in FIG. 9. Any appropriate sterilization method or agent may be used, for example ethylene oxide, gamma irradiation and steam under pressure, for example by autoclaving. It has been found to be particularly convenient to use gamma irradiation at levels of around 30 kgY.

Yet a further aspect of the invention comprises the use of one or more supporting structures attached perpendicularly to the tubular bandage at the point where the bandage is first rolled on to the body part. This is exemplified in FIGS. 10 to 13. Any suitable supportive material may be used, for example, thin wafers of plastic, provided that the material is sufficiently rigid or is otherwise constructed to act as a splint or support for the finger or other limb part. In the drawings, FIG. 10 shows a rolled finger bandage 12 to which a pair of splints 13 are attached, for example by means of adhesive 14 applied to an end of each splint (FIG. 11) for attachment inside the first roll of the bandage. FIG. 12 shows a splint 15 in the form of a U, the end 16 connecting the limbs thereof being secured within the first roll of the bandage by means of an adhesive 17 (FIG. 13).

The further improvement whereby the finger or limb around which the tubular bandage has been applied is dipped into a coating fluid, for example collodion, is also envisaged. This modification not only has the effect of rendering the bandage substantially impervious, but it also gives a measure of support to the part. Although many different coating materials may be used, collodion has been found to be particularly useful, being a solution of pyroxylin in alcohol and ether which when applied in thin layers evaporates to leave a tough film.

The present invention also concerns methods of manufacture of the tubular bandages as herein described and to the use of the hereinbefore-described tubular bandages.

In order to clarify further the various features of the present invention some explanatory technical background follows.

The tubular bandages of the invention are provided in individual units which will normally have been cut from a longer, manufactured length of tubular material, such as stockinette. As with current bandage material, the stockinette may be knitted in a range of tube diameters for use on different parts of the body and the lengths cut for the individual bandages of the invention may be gauged fairly accurately to cover the particular body part for which they are intended: this avoids the wastage of material which inevitably occurs when busy nurses have to judge the length required as and when it is needed. By way of example, tubular stockinette having a diameter of about 20 mm and a length of approximately 200 mm would be suitable for fingers while 60 mm diameter tube in lengths of about 500 mm would be suitable for forearms.

A bandage unit of the invention is preferably cut so that it is slightly longer than twice the length of the part to be covered so that the free ends of the bandage, when in place, are still slightly rolled: these rolls help to keep the bandage in place although plasters or other means may also be applied to ensure that the bandage is retained.

The material chosen for certain tubular bandages of the present invention comprises a knitted fabric incorporating courses of elastic yarn in addition to courses of substantially inelastic yarn. This is because the stockinette usually used for tubular bandages, which comprises plain-knitted inelastic yarn, does not roll easily and has little tendency to return to its original shape after stretching: the incorporation of the elastic yarn in the present bandages gives the fabric a certain resilience, in addition to that provided by the knitted structure, and makes it easier to roll and, once rolled, helps it remain in its rolled form.

The inelastic yarn may comprise any of the spun fibre yarns such as those currently used in bandage materials, including linen, cotton, viscose, polyester, cotton/viscose or cotton/polyester mixtures. The elastic yarn preferably comprises a yarn of the type generally known as a bulked yarn made, for example, from continuous filaments of polyamide or which may or may not be combined with an elastomeric fibre by any method of production such as covering airtexturing; such bulked yarns provide additional advantages to that of elasticity. In particular, they transmit fluids quickly and easily, are readily washable and dry quickly so that bandages incorporating them may be washed and re-used if necessary, although they would normally be thrown away after a single use. The combination of bulk and resilience of such yarns also makes the fabric knitted from them feel softer and more comfortable in use than the stockinette currently available. In particular, the resilience enables a tubular bandage of the invention made from this fabric to contract slightly around the bandaged part, thus providing radial support and pressure which can assist healing as well as helping to keep the bandage in place, although clearly a bandage must be selected so that it is not so tight as to restrict blood circulation and cause discomfort.

The knitted fabric incorporating elastic yarn used in the bandages of the invention preferably includes alternate courses of the elastic and inelastic yarns although fabrics may have a greater or lesser proportion of the elastic yarn as convenient for a particular use. The elasticated yarn is, in effect, layed in spirals at predetermined intervals.

It may be noted that the use of two yarns in the knitted fabric constituting the bandage has the further advantage of making the fabric much less easy to unravel, and therefore less liable to fray at a cut end, than conventional stockinette.

The various aspects of the present invention relate in addition to tubular bandages in which the yarn comprises fibres containing one or more antimicrobial compounds. These fibres, as disclosed in British Patent Application No. 9102280.6 dated 2 nd Feb. 1991, preferably comprise high performance acrylic or similar synthetic fibres either singly or as blends, containing a synergistic combination of antimicrobial compounds which ensure a wide spectrum of antimicrobial action. The active components are preferably metallic salts, for example salts of silver and zinc, each of which is known to be active in controlling the growth of bacteria and fungi. The antibacterial materials are bound within the fibre matrix to confer a high degree of activity which is not appreciably reduced by washing. This has obvious advantages over topically applied antimicrobial agents which can be readily removed in normal use and the antimicrobial performance of the fibres drastically reduced. Furthermore, acrylic fibres are resistant to microbial deterioration thereby giving more prolonged strength retention when woven into textile structures and reduced visual staining. Although the fabric would normally be plain-knitted stockinette, it could be constructed in alternative knitting stitches for specific purposes.

A further extension of the inventive concept of the present invention is the incorporation of a metallised yarn in a bandage fabric. Bandages made from the fabric may be detectable by metal detectors, such as those used, for example, in food-production lines to check for foreign bodies in the food produce. In this context, the metallised yarn need contain only 1% -2% by weight of metal, the fabric containing 0.5% by weight or less.

The metal incorporated in a bandage fabric, which must be sterilisable, is preferably stainless steel because of its general inertness although copper or other metals may be used when the requirements are less stringent.

We claim:

1. A tubular bandage comprising a length of tubular knitted fabric comprising one or more courses of substantially inelastic yarn interknitted with one or more courses of elastic yarn throughout said length, the tubular fabric having a first end portion rolled outwardly from the free end and the other end portion rolled inwardly from the opposite free end to form two rolls; and a dressing comprised of a separate material adapted to be applied directly to a wound attached to the said first end rolled portion of the fabric which is adapted to placed on top of said dressing.

2. A tubular bandage as claimed in claim 1, wherein said dressing comprises a material selected from the group comprising gauze, lint, tulle, fibre rovings, woven and non-woven fabric materials, sponge, foam and charcoal pads.

3. A tubular bandage as claimed in claim 1, wherein said dressing is impregnated with a material selected from chemical and biological agents.

4. A tubular bandage as claimed in claim 3, wherein said material is chemical and comprises a silicone.

5. A tubular bandage as claimed in claim 3, wherein said means is chemical and comprises an antimicrobial agent.

6. A tubular bandage as claimed in claim 3, wherein said material is chemical and comprises a dyestuff.

7. A tubular bandage as claimed in claim 3, wherein said material is chemical and is applied in the form of illustrative material.

8. A tubular bandage as claimed in claim 7, wherein said illustrative material is a logo.

9. A tubular bandage as claimed in claim 3, wherein said material is chemical and renders the bandage supportive.

10. A tubular bandage as claimed in claim 9, wherein said chemical material comprises collodion solution.

11. A tubular bandage as claimed in claim 1, further including a layer of non-toxic adhesive between said first end rolled portion of the said fabric and said dressing.

12. A tubular bandage as claimed in claim 1, wherein the knitted fabric has applied hereto a chemical agent to render the bandage resistant to the inward passage of fluids.

13. A tubular bandage as claimed in claim 12, wherein the chemical agent renders the bandage impervious to water.

14. A tubular bandage as claimed in claim 12, wherein the chemical agent renders the bandage impervious to oils.

15. A tubular bandage as claimed in claim 1, further including a supporting structure associated with the bandage.

16. A tubular bandage comprising a length of tubular knitted fabric comprising one or more courses of substantially inelastic yarn interknitted with one or more courses of elastic yarn throughout said length, the tubular fabric having a first end portion rolled outwardly from the free end and the other end portion rolled inwardly from the opposite free end to form two rolls;

a supporting structure; and means for attaching said supporting structure perpendicularly to said first end rolled portion of said fabric.

17. A tubular bandage as claimed in claim 16, wherein said supporting structure comprises a wafer of plastics material to act as a splint.

18. A tubular bandage as claimed in claim 16, wherein a pair of supporting structures are attached inside said first roll of said bandage.

19. A tubular bandage as claimed in claim 16, wherein said supporting structure comprises a U-shaped member in which the part bridging the limbs thereof is secured to said first roll of said bandage.

20. A tubular bandage comprising a length of tubular knitted fabric comprising one or more courses of substantially inelastic yarn interknitted with one or more courses of elastic yarn throughout said length, the bandage having a first end portion rolled outwardly from the free end and the other end portion rolled inwardly from the opposite free end to form two rolls, characterised in that a dressing is attached to said first end rolled portion of the bandage, the bandage further comprising a layer of non-toxic adhesive between said first end rolled portion of said bandage and the dressing.

* * * * *